United States Patent [19]

Rose et al.

[11] Patent Number: 4,900,325

[45] Date of Patent: Feb. 13, 1990

[54] HAIR-DYEING PREPARATIONS

[75] Inventors: David Rose, Hilden; Edgar Lieske, Duesseldorf; Norbert Maak, Neuss; Horst Hoeffkes, Duesseldorf-Hellerhof, all of Fed. Rep. of Germany

[73] Assignee: Henkel Kommanditgesellschaft auf Aktien, Duesseldorf, Fed. Rep. of Germany

[21] Appl. No.: 236,959

[22] Filed: Aug. 26, 1988

[30] Foreign Application Priority Data

Aug. 28, 1987 [DE] Fed. Rep. of Germany ....... 3728748

[51] Int. Cl.$^4$ ................................................. A61K 7/13
[52] U.S. Cl. ........................................... 8/408; 8/409; 8/410; 8/416; 8/423
[58] Field of Search ................... 8/408, 409, 416, 423, 8/429, 432, 431; 564/305, 442; 544/242

[56] References Cited

U.S. PATENT DOCUMENTS 4,200,432  4/1980  Kalopissis et al. ................... 8/11

FOREIGN PATENT DOCUMENTS 0195361  7/1978  European Pat. Off. .
294184   3/1979  European Pat. Off. .
2659056  6/1980  European Pat. Off. .
0176798  5/1985  European Pat. Off. .

OTHER PUBLICATIONS

Chemical Society, "Journal of the Chemical Society", 1948, London.

Kirk-Othmer; Encyclopedia of Chemical Technology, Third Edition, Volume 12, pp. 101–105.
Kirk-Othmer; Encyclopedia of Chemical Technology, vol. 8, p. 199.

Primary Examiner—Paul Lieberman
Assistant Examiner—John F. McNally
Attorney, Agent, or Firm—Ernest G. Szoke; Wayne C. Jaeschke; Norvell E. Wisdom, Jr.

[57] ABSTRACT

Hair-dyeing compositions containing oxidation dye precursors and a carrier contain coupler components corresponding to the formula:

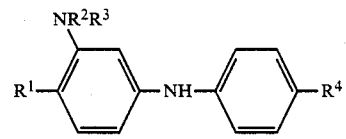

wherein $R^1$ is selected from the group consisting of hydrogen, a $C_1$–$C_4$ alkyl group or a halogen atom; $R^2$ and $R^3$ independently of one another are selected from the group consisting of hydrogen, $C_1$–$C_4$ alkyl groups or $C_2$–$C_4$ hydroxyalkyl groups, or together with the nitrogen atom, form a morpholine, piperidine, pyrrolidine or piperazine ring; and $R^4$ is selected from the group consisting of hydrogen or a —$NR^2R^3$ group; or salts thereof. The composition also contains typical developer components. The compounds are particularly suitable as red couplers for developers of the 2,4,5,6-tetraaminopyrimidine type, including derivatives thereof.

20 Claims, No Drawings

HAIR-DYEING PREPARATIONS

BACKGROUND OF THE INVENTION

1. Field of the Invention

This invention relates to hair-dyeing preparations based on oxidation dyes.

2. Statement of Related Art

Hair-dyeing preparations containing oxidation dye precursors dispersed in a cosmetic carrier are known in the art. The oxidation dye precursors present in such preparations are developer substances and coupler substances which form dyes under the effect of oxidizing agents or atmospheric oxygen. The cosmetic carriers used for the oxidation dye precursors include creams, emulsions, gels, shampoos, foam aerosols or other preparations suitable for application to the hair.

By virtue of their intense colors and good fastness properties, so-called oxidation hair dyes play a prominent part in the dyeing of hair. Oxidation dyes are formed by the oxidative coupling of one or more developer components with one another or with one or more coupler components. The developer substances commonly used are primary aromatic amines containing another free or substituted hydroxy or amino groups in the para position or ortho position, as well as diaminopyridine derivatives, heterocyclic hydrazone derivatives, 4-aminopyrazolone derivatives, and tetraaminopyrimidines. The so-called coupler substances commonly used are m-phenylenediamine derivatives, naphthols, resorcinol derivatives and pyrazolones.

Good oxidation dye precursors must satisfy certain primary requirements. They must form the desired shades of color with sufficient intensity during the oxidative coupling reaction. In addition, they must be readily absorbed by human hair without excessively staining the scalp. Dye absorption should also be uniform, i.e., the more heavily stressed ends should not be dyed to a greater extent than the less damaged hairline. The dye finishes produced using such precursors should be highly stable to heat, light and the chemicals used in the permanent waving of hair. Finally, the oxidation hair dye precursors should be safe to use from the toxicological and dermatological standpoint.

Aminodiphenylamines of a different chemical structure are known in the art as oxidation dye precursors, as disclosed for example in German patent document DE-PS 294 184 and in U.S. Pat. No. 4,200,432. However, the hair-dyeing preparations prepared with these products are unsatisfactory in regard to the fastness properties of the dye finishes obtained. In particular, these amoinodiphenylamines are not suitable as red couplers for developer components of the 2,4,5,6-tetraaminopyrimidine type either because they do not form red shades with developers of this type or because the shades formed are absorbed too unevenly. Also, these materials tend to color the hair ends to a greater extent than the less damaged, newer hairline regions closer to the hair roots. This disadvantage appears to be common to all known red couplers for developers of the tetraaminopyrimidine type.

DESCRIPTION OF THE INVENTION

Other than in the operating examples, or where otherwise indicated, all numbers expressing quantities of ingredients or reaction conditions used herein are to be understood as modified in all instances by the term "about".

It has now been discovered that the aforementioned requirements of oxidation dye precursor formulations may be satisfied to a high degree by preparing a composition comprising developer components and an oxidation dye precursor having the formula I:

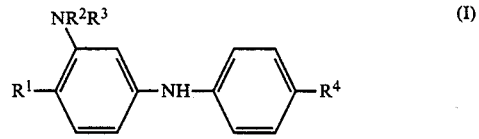

wherein $R^1$ is selected from the group consisting of hydrogen, a $C_1$-$C_4$ alkyl group or a halogen atom; $R^2$ and $R^3$ independently of one another are selected from the group consisting of hydrogen, $C_1$-$C_4$ alkyl groups or $C_2$-$C_4$ hydroxyalkyl groups, or together with the nitrogen atom, form a morpholine, piperidine, pyrrolidine or piperazine ring; and $R^4$ is selected from the group consisting of hydrogen or a $-NR^2R^3$ group; or salts thereof.

The aminophenylamines corresponding to formula (I) are suitable as couplers for a number of known developer compounds and produce particularly bright colors showing high stability to light and heat. The developers present in the hair-dyeing preparations according to this invention include aromatic amines containing one or more other $NH_2$ groups, NHR groups, $NR_2$ groups, where R is a $C_1$-$C_4$ alkyl group or a $C_2$-$C_4$ hydroxyalkyl group or a $C_2$-$C_4$ aminoalkyl group; aminophenols; aminophenol ethers; diaminopyridine derivatives; or 2,4,5,6-tetraaminopyrimidine, and derivatives thereof. Preferred are those aminodiphenylamines of formula (I) in which $R^1$ is hydrogen, a methyl group or chlorine, $R^2$ and $R^3$ independently of one another represent hydrogen or a methyl group and $R^4$ is hydrogen or an amino group.

The aminodiphenylamines corresponding to formula (I) are generally known in the literature or may be obtained by methods known in the literature. The preparation of 3-amino-4-chlorodiphenylamine hydrochloride, which is not known in the literature, is described in Example 1. This compound is prepared using the so-called ULLMANN reaction by reacting 4-chloro-3-nitroacetanilide and bromobenzene in the presence of sodium carbonate, potassium iodide and copper powder at elevated temperature, followed by reduction of the nitro group to the amino group. Other aminodiphenylamines corresponding to formula (I) may be prepared by the same method.

The aminodiphenylamines corresponding to formula (I) are particularly suitable coupler components for developers of the 2,4,5,6-tetraaminopyrimidine type, including derivatives thereof, because they exhibit particularly good levelling power. They form red or brown-red shades with these developer components which are absorbed particularly uniformly by the hair in the region of the hair-line and the hair ends. A comparison of the levelling power of the hair-dyeing preparation according to this invention, containing 5-dimethylamino-4'-aminodiphenylamine as coupler and 2,4,5,6-tetraaminopyrimidine as developer, with that of an otherwise identical hair-dyeing preparation of the prior art containing 2-methyl resorcinol as a red coupler for 2,4,5,6-tetraminopyrimidine shows that, with the hair-dyeing preparation according to the invention, the difference in color between a dyed, damaged strand of hair and a dyed, undamaged strand of hair is reduced to less than half the value obtainable with the conventional hair-dyeing preparation containing 2-methyl resorcinol as coupler.

In a particularly preferred embodiment, the present invention relates to hair-dyeing preparations containing, as a developer, a 2,4,5,6-tetraaminopyrimidine or derivatives thereof corresponding to the following formula:

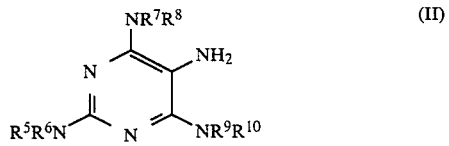

wherein $R^5$ to $R^{10}$ independently of one another are selected from the group consisting of hydrogen, $C_1$–$C_4$ alkyl groups and $C_2$–$C_4$ hydroxyalkyl groups, or the groups $R^5$ and $R^6$, or $R^7$ and $R^8$, or $R^9$ and $R^{10}$, together with the nitrogen atom, form a morpholine, piperidine, pyrrolidine or piperazine ring, or salts thereof.

2.4.5.6-tetraaminopyrimidine is the preferred developer component corresponding to formula (II). The aminodiphenylamines corresponding to formula (I) and the tetraaminopyrimidines corresponding to formula (II) may be present in the hair-dyeing preparations of this invention either in free form or in the form of amino salts with inorganic or organic acids, including the hydrochlorides, sulfates, phosphates, acetates, propionates, lactates or citrates.

In addition to the aminodiphenylamines corresponding to general formula (I), the hair-dyeing preparations according to this invention may also contain other couplers known in the prior art which are used either for modifying the shades or for producing natural hues. Known couplers of this type include other n-phenylene diamines such as 2,4-diaminophenyl-2-hydroxyethyl ether, 2,4-diaminoanisole as well as phenols, resorcinols, m-aminophenols, naphthols or pyrazolones. For example, to produce natural blond, brown or black hair colors using an oxidation hair-dyeing preparation containing a developer of the 2,4,5,6-tetraamino pyrimidine type corresponding to formula (II), it is necessary, in addition to the red couplers of the aminodiphenylamine type corresponding to formula (I), to also use yellow couplers and/or blue couplers for this developer, which also readily absorbed dyes of high levelling power with tetraamino pyrimidines. Particularly suitable yellow couplers include 2,7-dihydroxynaphthalene and 2,6-dihydroxy-3,4-di methylpyridine. One example of a particularly preferred blue coupler is 2-methyl-5-amino-6-chlorophenol.

In a particularly preferred embodiment, the invention relates to a hair-dyeing preparation containing a 2,4,5,6-tetraaminopyrimidine as a developer component and also containing one or more couplers selected from the group consisting of 2,7-dihydroxynaphthalene, 2,6-dihydroxy-3,4-dimethylpyridine, 2-methyl-5-amino-6-chlorophenol and mixtures thereof, in addition to the aminodiphenylamines corresponding to formula (I).

Substantive dyes may be additionally present in the hair-dyeing compositions of this invention for the purpose of further modifying the shades. Suitable substantive dyes include nitrophenylenediamines, nitroaminophenols, anthraquinone dyes or indophenols.

To prepare the hair-dyeing preparations according to this invention, the aminodiphenylamines corresponding to formula (I) and other couplers additionally present, if any, are generally present in substantially equi-molar quantities with the developer components used. Although it is preferred to use equi-molar quantities, a certain excess of individual oxidation dye precursors is not a disadvantage. Developer components and coupler components may be present in a molar ratio of from 1:0.5 to 1:2 respectively.

The aminodiphenylamines corresponding to formula (I) and other oxidation dye precursors or substantive dyes which may be present, and the developers present in the hair-dyeing preparations of this invention do not have to be individual chemical compounds. Mixtures of one or more couplers and/or one or more developers may also be used in accordance with this invention.

The hair color may be oxidatively developed either with atmospheric oxygen or preferably using a chemical oxidizing agent. The latter technique is particularly preferred when it is desired not only to color the hair but also to lighten it. Particularly preferred oxidizing agents include hydrogen peroxide or adducts thereof with urea, melamine or sodium borate, as well as mixtures of hydrogen peroxide or such hydrogen peroxide adducts with potassium peroxydisulfate. Such oxidizing agents are preferably added to the hair-dying composition as dilute aqueous solutions containing about 1–20% by weight of $H_2O_2$, at a level within the range of 50 to 200% by weight of the dying preparation.

The hair-dyeing composition (or preparation) of this invention may be produced by incorporating the oxidation dye precursors into a suitable cosmetic carrier. Examples of suitable cosmetic carriers include creams, emulsions, gels and surfactant-containing foaming solutions such as shampoos, as well as other carrier formulations which are suitable for application to the hair. Standard ingredients present in such cosmetic preparations including wetting agents and emulsifiers, such as anionic, nonionic or ampholytic surfactants. Examples of such wetting agents and surfactants include fatty alcohol sulfates, alkanesulfonates, alpha-olefinsulfonates, fatty alcohol polyglycol ether sulfates, ethylene oxide adducts with fatty alcohols, fatty acids and alkylphenols, sorbitan fatty acid esters and fatty acid partial glycerides, and fatty acid alkanolamides. The preparation may also contain thickeners such as methyl or hydroxyethyl cellulose; starch; fatty components such as fatty alcohols; paraffin oils; fatty acid esters; perfume oils; and hair-care additives including water-soluble cationic polymers, protein derivatives, pantothenic acid and cholesterol.

The constituents of the cosmetic carriers are present in the usual quantities in the hair-dyeing compositions of this invention. For example, emulsifiers may be present in concentrations of 0.5 to 30% by weight and thickeners may be present concentrations of 0.1 to 25% by weight, based on the weight of the hair-dyeing composition as a whole.

A particularly preferred carrier is an oil-in-water emulsion containing 0.1 to 25% by weight of a fatty component and 0.5 to 30% by weight of an emulsifier selected from the group consisting of anionic, nonionic or ampholytic surfactants.

The oxidation dye precursors are present in the composition in quantities of 0.2 to 5% by weight and preferably in quantities of 1 to 3% by weight, based on the weight of the hair-dyeing composition as a whole. The content of aminodiphenylamines of formula (I) in the hair-dyeing composition may be from 0.05 to 10 millimol per 100 g of the hair-dyeing composition.

The hair-dyeing compositions according to this invention are preferably mildly alkaline, irrespective of the form of the cosmetic preparation, for example a cream, gel or shampoo. The hair-dyeing compositions preferably have a pH value in the range from 8 to 10. and are preferably applied to the hair at a temperature with the range from 15° C. to 40° C. After a contact time of about 30 minutes, the hair-dyeing composition is removed from the hair by rinsing. The hair is then preferably washed with a mild shampoo and dried. Washing with a carrier of high surfactant content is used, such as a dye shampoo.

The following Examples are intended to illustrate the invention without limiting it in any way.

EXAMPLE 1

(a) Preparation of 3-amino-4-chlorodiphenylamine hydrochloride coupler

Step 1: 3-nitro-4-chlorodiphenylamine

A mixture consisting of 4-chloro-3-nitro acetanilide (23 g), bromobenzene (34 g), sodium carbonate (8.1 g), potassium iodide (0.4 g) and copper powder (0.24 g) in 125 ml nitrobenzene was heated to 180°–200° C. and maintained at that temperature for 18 hours. After removal of the nitrobenzene by steam distillation, the oily residue was isolated from the aqueous phase and heated with dilute hydrochloric acid to the boiling temperture. After 3 hours, the reaction mixture was poured onto cold water and the precipitated product was isolated.

Step 2:

The crude 3-nitro-4-chlorodiphenylamine produced in Step 1 was reacted with hydrogen gas in ethanol in the presence of catalytic quantities of Raney nickel. When the uptake of hydrogen was over, the solution was filtered off from the catalyst and acidified with dilute hydrochloric acid. Dark grey crystals were obtained after concentration of the solution to dryness.

(b) Hair dye composition and application technique

Hair-dyeing compositions according to the invention were prepared in the form of a cream emulsion having the following composition:

| | |
|---|---|
| $C_{12}$—$C_{18}$ fatty alcohol | 10 g |
| $C_{12}$—$C_{14}$ fatty alcohol + 2 EO sulfate, Na salt, 28% | 25 g |
| Water | 60 g |
| 2,4,5,6-tetraaminopyrimidine | 7.5 mmol |
| 3-amino-4-chlorodiphenylamine of step 2 above | 7.5 mmol |
| $Na_2SO_3$ (inhibitor) | 1.0 g |

'The constituents were mixed together in the above order. After addition of the oxidation dye precursors and the inhibitor, the pH value of the emulsion was first adjusted to 9.5 with concentrated ammonia solution, after which the emulsion was made up with water to give 100 g. of total composition.

The hair color was oxidatively developed with 3% hydrogen peroxide solution as the oxidizing agent by adding 50 g of hydrogen peroxide solution to 100 g of the emulsion and mixing.

The dye cream was applied to approximately 5 cm long strands of standardized, 90% grey, but not specially pretreated human hair and left thereon for 30 minutes at 27° C. After dyeing, the hair was rinsed, washed with a standard shampoo and then dried.

EXAMPLES 2–17

Sixteen additional hair-dyeing compositions were prepared and applied to the hair as set forth in part (b) of Example 1 above, except that various combinations of couplers (C) and developers (D) were used. These couplers and developers are identified below, and the combinations employed are set forth in Table 1. Table 1 also describes the hair shades obtained using the various combinations of couplers and developers.

Couplers:
C1: 3-amino-4-chlorodiphenylamine (Example 1)
C2: 3-amino-4-methyl diphenylamine (disclosed in German patent 80977)
C3: 3-aminodiphenylamine (disclosed in J. Chem. Soc. (1948), 1228)
C4: 3-dimethylamino-4'-aminodiphenylamine (disclosed in J. Chem. Soc. (1948), 1229)
C5: 3,4'-diaminodiphenylamine (disclosed in J. Chem. Soc. (1948), 1229)

Developers:
D1: 2,4,5,6-tetraaminopyrimidine
D2: 2-methylamino-4,5,6-triaminopyrimidine
D3: 2-dimethylamino-4,5,6-triaminopyrimidine
D4: 2-piperidyl-4,5,6-triaminopyrimidine
D5: 2-morpholino-4,5,6-triaminopyrimidine
D6: 2,5-diaminotoluene.

TABLE 1

| Application Example | Developer Component | Coupler Component | Shade Obtained |
|---|---|---|---|
| 1 | D1 | C1 | Light Brown |
| 2 | D4 | C1 | Red-Brown |
| 3 | D5 | C1 | Red-Brown |
| 4 | D1 | C2 | Orange-Brown |
| 5 | D2 | C2 | Brown-Red |
| 6 | D3 | C2 | Brown-Red |
| 7 | D4 | C2 | Brown-Red |
| 8 | D5 | C2 | Brown-Red |
| 9 | D1 | C3 | Titian Red |
| 10 | D2 | C3 | Red-Brown |
| 11 | D1 | C4 | Port Red |
| 12 | D1 | C5 | Red-Brown |
| 13 | D6 | C1 | Ruby |
| 14 | D6 | C2 | Burgundy Red |
| 15 | D6 | C3 | Black-Violet |
| 16 | D6 | C4 | Blue-Violet |
| 17 | D6 | C5 | Black-Blue |

It is to be understood that the above described embodiments of the invention are illustrative only and that modifications throughout may occur to those skilled in the art.

We claim:

1. A hair dyeing composition containing as oxidation dye precursors, in a total amount between about 0.2 to about 5% by weight of the total composition, a developer component and a coupler component in amounts such as to give a molar ratio between said developer component and said coupler component in the range between about 0.5:1 to about 2:1, both of said oxidation dye precursors being dispersed in an aqueous-based carrier, said coupler component comprising between about 0.05 and about 10 millimoles per 100 grams of total composition of molecules having the formula:

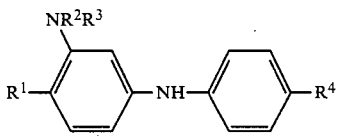

wherein $R^1$ is selected from the group consisting of hydrogen, a $C_1$–$C_4$ alkyl group and a halogen atom; $R^2$ and $R^3$ independently of one another are selected from the group consisting of hydrogen, $C_1$–$C_4$ alkyl groups and $C_2$–$C_4$ hydroxyalkyl groups or, together with the nitrogen atom, form a morpholine, piperidine, pyrrolidine or piperazine ring; and $R^4$ is selected from the group consisting of hydrogen or a —$NR^2R^3$ group; and salts thereof.

2. The composition of claim 1 wherein $R^1$ is hydrogen, methyl or chloro, $R^2$ and $R^3$ independent of one another are hydrogen or methyl, and $R^4$ is hydrogen or amino.

3. The composition of claim 1 wherein said coupler component is selected from the group consisting of 3-amino-4-chlorodiphenylamine, 3-amino-4-methyl diphenylamine, 3-aminodiphenylamine, 3-dimethylamino-4'-aminodiphenylamine, 3,4'-diaminodiphenylamine, and mixtures thereof.

4. The composition of claim 3 wherein said coupler component is 3-amino-4-chlorodiphenylamine.

5. The composition of claim 1 wherein said developer is a 2,4,5,6-tetraamino-pyrimidine having the formula:

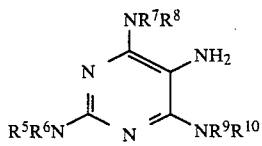

wherein $R^5$ to $R^{10}$ independent of one another are selected from the group consisting of hydrogen, $C_1$–$C_4$ alkyl groups and $C_2$–$C_4$ hydroxyalkyl groups, or the groups $R^5$ and $R^6$, or $R^7$ and $R^8$, or $R^9$ and $R^{10}$, together with the nitrogen atom, form a morpholine, piperidine, pyrrolidine or piperazine ring, or salts thereof.

6. The composition of claim 5 wherein said developer is selected from the group consisting of 2,4,5,6-tetraminopyrimidine, 2-methylamino-4,5,6-triaminopyrimidine, 2-dimethylamino-4,5,6-triaminopyrimidine, 2-piperidyl-4,5,6-triaminopyrimidine, and 2-morpholino-4,5,6-triaminopyrimidine.

7. The composition of claim 6 wherein said developer is 2,4,5,6-tetraaminopyrimidine.

8. The composition of claim 5 further containing one or more couplers selected from the group consisting of 2,7-dihydroxynaphthalene, 2,6-dihydroxy-3,4-dimethylpyridine and 2-methyl-5-amino-6-chlorophenol.

9. The composition of claim 1 wherein said oxidation dye precursors are present at a level of about 1 to about 3% by weight of said hair-dyeing composition.

10. The composition of claim 1 wherein said developer component and said coupler component are present in approximately equi-molar amounts.

11. The composition of claim 1 wherein said developer is 2,5-diaminotoluene.

12. The composition of claim 5 further containing an oxidizing agent.

13. The composition of claim 5 further containing a substantive dye.

14. The composition of claims 1 or 5 in the form of an oil-in-water emulsion containing from about 0.5 to about 30% by weight of an emulsifier selected from the group consisting of anionic, nonionic and ampholytic surfactants.

15. The composition of claim 14 further containing from about 0.1 to about 25% by weight of a fatty component.

16. The composition of claim 5 wherein said coupler component consists essentially of 3-amino-4-chlorodiphenyl amine and said developer is selected from the group consisting of 2,4,5,6-tetraminopyrimidine, 2-methylamino-4,5,6-triaminopyrimidine, 2-dimethylamino-4,5,6-triaminopyrimidine, 2-piperidyl-4,5,6-triaminopyrimidine, and 2-morpholino-4,5,6triaminopyrimidine.

17. The composition of claim 16 wherein said developer component is 2,4,5,6-tetraaminopyrimidine.

18. The composition of claim 14 having a pH of from about 8 to about 10.

19. The composition of claim 14 further containing an oxidizing agent.

20. A method for dyeing the hair comprising contacting or washing the hair with the composition of claims 1, 5 or 14, allowing said composition to remain in the hair for a period of time sufficient to color the hair, and removing said composition from the hair.

* * * * *